United States Patent
Hunkeler et al.

(10) Patent No.: US 9,144,465 B2
(45) Date of Patent: Sep. 29, 2015

(54) TRANSPORT CARRIER FOR SYRINGES

(71) Applicant: Fisher Clinical Services GmbH, Allschwil (CH)

(72) Inventors: Guido Hunkeler, Schonenbuch (CH); Ulrich Gerstmann, Allschwil (CH)

(73) Assignee: Fisher Clinical Services GmbH, Allschwil (CH)

( * ) Notice: Subject to any disclaimer, the term of this patent is extended or adjusted under 35 U.S.C. 154(b) by 0 days.

(21) Appl. No.: 13/870,417

(22) Filed: Apr. 25, 2013

(65) Prior Publication Data

US 2013/0306513 A1    Nov. 21, 2013

(30) Foreign Application Priority Data

May 8, 2012 (CH) ......................... 638/12

(51) Int. Cl.
*A61B 19/02* (2006.01)
*A61M 5/00* (2006.01)
*A61M 5/28* (2006.01)
*A61M 5/315* (2006.01)
*B65D 81/113* (2006.01)
*A61M 5/31* (2006.01)

(52) U.S. Cl.
CPC .............. *A61B 19/026* (2013.01); *A61M 5/002* (2013.01); *A61M 5/008* (2013.01); *A61M 5/28* (2013.01); *A61M 5/31501* (2013.01); *B65D 81/113* (2013.01); *A61M 2005/3117* (2013.01)

(58) Field of Classification Search
CPC .... A61B 19/026; A61M 5/002; A61M 5/008; A61M 5/28; A61M 5/31501; A61M 2005/3117; B65D 81/107; B65D 81/1075; B65D 81/113

USPC .......................... 206/364–366, 438, 523, 571
See application file for complete search history.

(56) References Cited

U.S. PATENT DOCUMENTS

| | | | | |
|---|---|---|---|---|
| 4,524,868 A * | 6/1985 | Buckley et al. | ................ | 206/364 |
| 4,657,138 A * | 4/1987 | Watson | ........................ | 206/366 |
| 4,753,345 A | 6/1988 | Goodsir et al. | | |
| 5,078,267 A * | 1/1992 | Wright | .......................... | 206/364 |
| 6,368,305 B1 | 4/2002 | Dutton | | |
| 7,806,265 B2 * | 10/2010 | Timm | ........................... | 206/438 |
| 8,186,513 B2 * | 5/2012 | St. John et al. | ................ | 206/495 |
| 2008/0255520 A1 | 10/2008 | Henderson | | |

FOREIGN PATENT DOCUMENTS

| | | |
|---|---|---|
| CH | 360168 | 2/1962 |
| DE | 85 30 003 U1 | 12/1985 |
| EP | 2 130 561 A1 | 12/2009 |
| WO | WO 01/23017 A2 | 4/2001 |

OTHER PUBLICATIONS

International Search Report issued Feb. 13, 2013, in Swiss Patent Application No. 6382012, filed May 8, 2012 (with English Translation of Categories of Cited Documents).

* cited by examiner

*Primary Examiner* — Bryon Gehman
(74) *Attorney, Agent, or Firm* — Oblon, McClelland, Maier & Neustadt, L.L.P.

(57) ABSTRACT

The carrier for prefilled syringes has a body made from a dimensionally stable elastic material with a chamber for inserting the syringe. The flange of the syringe cylinder is fixed in the axial direction in a defined recess, whereas the syringe plunger is fixed in any position in an elongated recess.

4 Claims, 3 Drawing Sheets

TRANSPORT CARRIER FOR SYRINGES

The invention relates to a carrier for syringes.

In the case of prefilled syringes, the nozzle serving for connecting to the injection needle, i.e., in most cases of the Luer-Lock type or Luer-Slip type, is usually closed for storing and transporting with a plug or the like so as to ensure sterility of the content and to prevent leakages. However, it was found that in certain situations, e.g., due to pressure differences during the air transport, displacements of the plunger can occur, which are disadvantageous in a number of respects. This concerns primarily also the sterility of the content because the region on the back of the plunger is not sterile. Thus, when a plunger moves due to changes in ambient pressure, the sterility of the syringe content can be at risk, even if the plunger is at the same position again after a movement.

It is an object of the invention to prevent accidental plunger movements in prefilled syringes during storage and transport.

This is achieved according to the invention by a transport carrier with the characterizing features of the claim 1.

A preferred exemplary embodiment of the invention is described hereinafter with reference of the accompanying drawings. In the figures.

Figure 1:
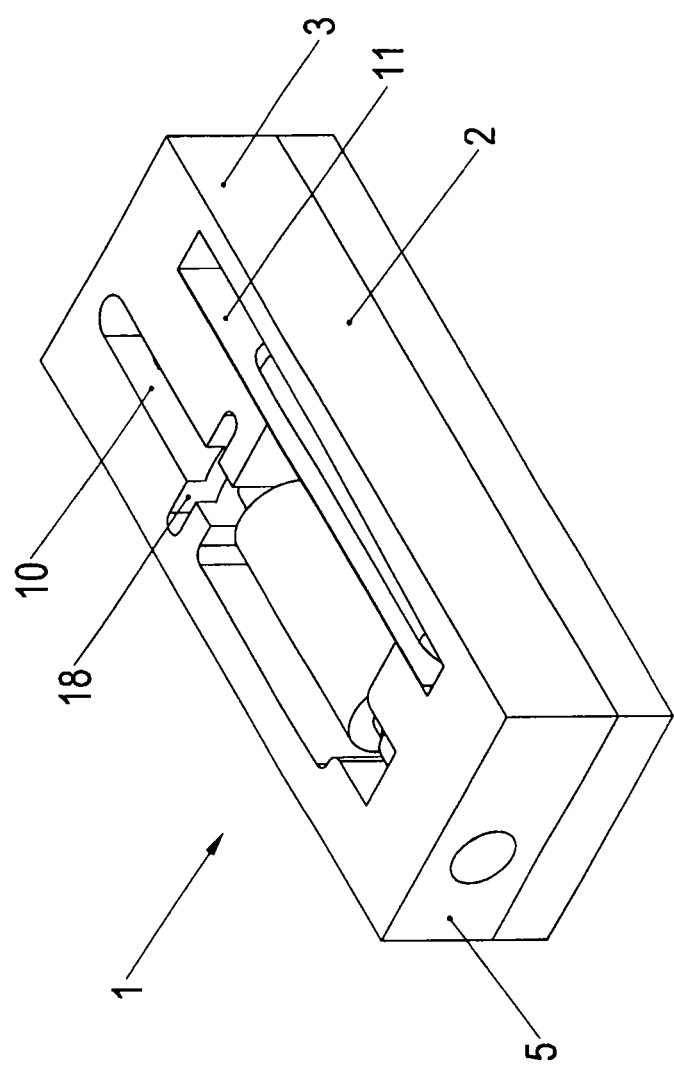
FIG. 1 shows a perspective illustration of a carrier with an inserted syringe.
Figure 2:
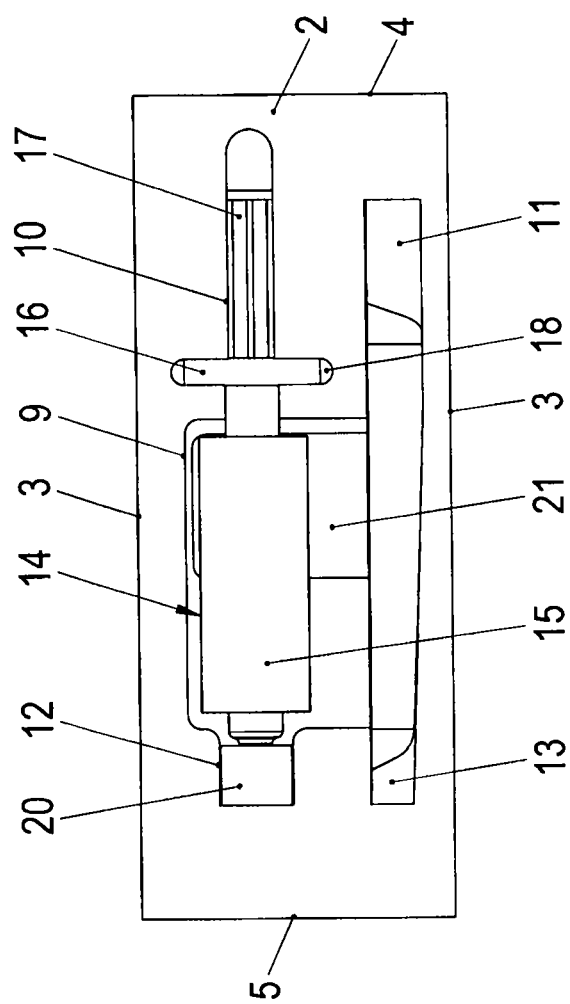
FIG. 2 shows a top view of the carrier with an inserted syringe.
Figure 3:
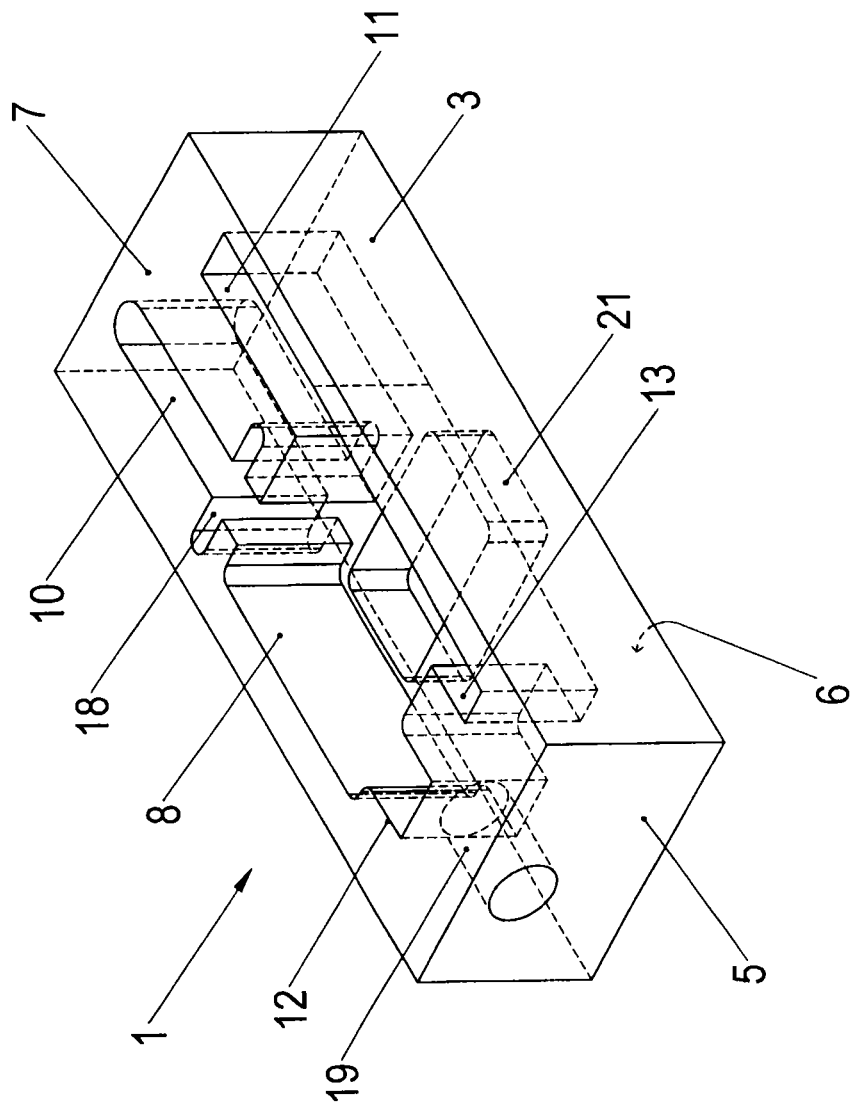
FIG. 3 shows a perspective illustration of the carrier with all contours extending in its interior.

The carrier 1 shown in the Figures has the outer shape of an elongated cuboidal body 2 with two closed sidewalls 3 opposing each other, a likewise closed front side, hereinafter designated as plunger-side front side 4, a second front side, hereinafter designated as needle-side front side 5, a lower side 6 and an upper side 7.

From the upper side, a chamber 8 extends into the interior of the body. The chamber comprises a center region 9 that is approximately rectangular in top view, from which center region extend in the plunger-side direction of the body two narrow elongated recesses 10, 11, and on the needle side extend shorter recesses 12, 13 which define with the latter the same center planes.

The recesses 10, 12 opposing each other on one side of the body serve with the corresponding portion of the center region 9 for accommodating a syringe 14, wherein the syringe cylinder 15 is accommodated in the center region, and the flange 16 of the cylinder and the plunger rod 17 are accommodated in the plunger-side recess 10. For accommodating the flange, a slot 18 is provided, which is arranged transverse to the longitudinal direction. The chamber is deep enough for accommodating the syringe completely.

From the needle-side recess 12, a cylindrical indentation 19 extends in the needle-side direction, which indentation is coaxial to the inserted syringe. For production-related reasons, this indentation is continuous up to the needle-side front side.

This indentation has a diameter corresponding to the sealing plug 20 and accommodates the sealing plug of the inserted syringe completely or partially. Of course, a different shape, e.g., slots or the like, can also serve for accommodating the sealing plug.

In the plunger-side half of the center region 9 there is provided an opening 21 toward the lower side of the body, which opening serves for removing the syringe from the carrier. Depending on the provisions taken for removing the syringe, the opening 21 can optionally be dispensed with.

The two other opposing recesses 11, 13 serve together with the corresponding portion of the center region as a chamber for accommodating a cannula to be used with syringe.

The body 2 in the present exemplary embodiment consists of high-density foam, for example Ethafoam®. Another material with similar properties can also be used.

When placing a prefilled syringe into the carrier, the syringe is first inserted with the sealing plug into the coaxial indentation and is then inserted with the flange into the transverse slot 18. Thereby, the syringe cylinder is fixed in the axial direction. When inserting the flange into the transverse slot, the plunge is pressed into the corresponding recess at the same time. In the process of this, the flange-shaped widening at the end of the plunger rod is also pressed between the walls of the recess and is fixed in the axial direction. For this purpose, the recess is narrower than the width of the end of the plunger rod.

Due to the fact that the flange-shaped widening of the plunger rod is held between the side walls of the recess without a defined axial position being provided for this, syringes having different filling levels and correspondingly different plunger positions can be held in the same carrier.

Removing the syringe from the carrier is carried by pushing the syringe upward through the opening below. Since the plug is held in the indentation, the needle side of the syringe cannot be moved transverse to its axis, but the flange-shaped end of the plunger rod and the flange of the syringe cylinder have first to be pushed out of the recess before the syringe cylinder can be removed in the axial direction from the indentation. In this manner it is ensured that no undesirable plunger displacement can take place during the removal. Of course, the order of the steps when inserting and/or removing the syringe can also take place differently.

Tests that have been carried out have shown that with the carrier according to the invention and with this fixing of a syringe, an axial movement of the plunger due to pressure differences or other uncontrolled influences can be reliably prevented.

Of course, when applying the inventive idea, other embodiment variants are obvious. Thus, it is possible to provide a carrier that has no receptacle for a cannula, but accommodates only the syringe. For removing, there are also possible variants, for example a strap lying underneath the syringe for lifting the flange or plunger side or a widening of the chamber next to the syringe cylinder, instead of the opening toward the lower side.

The invention claimed is:

1. A carrier for a prefilled syringe including a syringe cylinder including a flange and a plunger inside the cylinder and including a plunger rod, comprising:
    a body made from a dimensionally stable elastic material; and
    a chamber to receive the syringe, the chamber including
        a recess fixing a position of the flange of the received syringe cylinder in an axial direction of the received syringe, and
        an elongated recess of the chamber, the plunger rod being pressed between walls of said elongated recess and the elongated recess fixing a position of the plunger rod of the received syringe in any position in the axial direction.

2. The syringe carrier according to claim 1, wherein the elongated recess is narrower than a flange-shaped widening at an end of the plunger rod such that the plunger is axially fixed.

3. The syringe carrier according to claim 1, wherein a region to hold a cannula is provided in the chamber.

4. The syringe carrier according to claim 1, wherein a width of the elongated recess in a direction perpendicular to the axial direction is less than a corresponding width of a portion of the recess that receives the syringe cylinder.

* * * * *